(12) United States Patent
Mamiya

(10) Patent No.: US 8,436,890 B2
(45) Date of Patent: May 7, 2013

(54) THREE-DIMENSIONAL MEASURING DEVICE AND BOARD INSPECTION DEVICE

(75) Inventor: Takahiro Mamiya, Aichi (JP)

(73) Assignee: CKD Corporation, Aichi (JP)

( * ) Notice: Subject to any disclaimer, the term of this patent is extended or adjusted under 35 U.S.C. 154(b) by 784 days.

(21) Appl. No.: 12/669,433

(22) PCT Filed: Jul. 18, 2008

(86) PCT No.: PCT/JP2008/062985
§ 371 (c)(1),
(2), (4) Date: Jan. 15, 2010

(87) PCT Pub. No.: WO2009/019966
PCT Pub. Date: Feb. 12, 2009

(65) Prior Publication Data
US 2010/0194855 A1    Aug. 5, 2010

(30) Foreign Application Priority Data
Aug. 8, 2007  (JP) ................................ 2007-206112

(51) Int. Cl.
*H04N 13/00* (2006.01)
(52) U.S. Cl.
USPC ................................ 348/42; 382/154; 356/27
(58) Field of Classification Search .................... None
See application file for complete search history.

(56) References Cited

U.S. PATENT DOCUMENTS 6,075,605 A * 6/2000 Futamura et al. ............. 356/608
2002/0164066 A1* 11/2002 Matsumoto ................... 382/154

FOREIGN PATENT DOCUMENTS

| JP | 64-54208 A | 3/1989 |
|---|---|---|
| JP | 5-332737 A | 12/1993 |
| JP | 11-148810 A | 6/1999 |
| JP | 11-211443 A | 8/1999 |
| JP | 2001-243468 A | 9/2001 |
| JP | 2002-081924 A | 3/2002 |
| JP | 2005-003409 A | 1/2005 |
| JP | 2005-091176 A | 4/2005 |
| JP | 2006-177781 A | 7/2006 |
| JP | 2007-192608 A | 8/2007 |

OTHER PUBLICATIONS

International Search Report issued in PCT/JP2008/062985, mailed on Sep. 16, 2008, with translation, 4 pages.
International Search Report issued in PCT/JP2008/062985, mailed on Sepember 16, 2008, with translation, 4 pages.

\* cited by examiner

*Primary Examiner* — Christopher S Kelley
*Assistant Examiner* — Mohammed Jebari
(74) *Attorney, Agent, or Firm* — Osha Liang LLP

(57) ABSTRACT

A three-dimensional measuring device includes an irradiation means capable of irradiating a striped light pattern used for a spatial encoding method and a striped light pattern used for a phase shift method on a measurement object part on a board main body, an imaging means capable of imaging a measurement object part irradiated by the light pattern, an image control means for controlling imaging by the imaging means, a first calculation means for calculating a height of the measurement object part according to the phase shift method based on a multiplicity of image data imaged by the imaging means, and a second calculation means capable of using the spatial encoding method to identify a line corresponding to the measurement object part from among the image data at a time of calculation by the first calculation means by the phase shift method based on the image data.

20 Claims, 9 Drawing Sheets space encoding method imaging count = 0, height range = 0 μm~100 μm space encoding method imaging count = 2, height range = 100 μm~200 μm

THREE-DIMENSIONAL MEASURING DEVICE AND BOARD INSPECTION DEVICE

CROSS-REFERENCE TO RELATED APPLICATIONS

This application is a national stage application of International Application No. PCT/JP2008/062985 filed on Jul. 18, 2008, which claims priority to Japanese Patent Application No. 2007-206112 filed on Aug. 8, 2007 in Japan.

BACKGROUND OF INVENTION

1. Field of the Invention

The present invention relates to a three-dimensional measuring device and a board inspection device equipped with this three-dimensional measuring device.

2. Background Art

When an electronic component is mounted on a printed circuit board, a cream solder is generally first printed on a specific electrode pattern disposed on the printed circuit board. Adhesivity of this cream solder is then used to temporarily fix the electronic component on the printed circuit board. Thereafter, the above-described printed circuit board is conveyed to a reflow furnace, and soldering is performed by a routine reflow process. Recently, it has become necessary to perform an inspection of the printed state of the cream solder at a stage prior to conveyance to the reflow furnace, and three-dimensional measuring devices have been used for such inspection.

Various types of so-called non-contact type three-dimensional measuring devices using light have been proposed in recent years. Among these types, technology has been proposed that relates to three-dimensional measuring devices utilizing the phase shift method (e.g., see Patent Citation 1 and the like). In a three-dimensional measuring device using this phase shift method, an irradiation means is used that combines a light source and a sine wave pattern filter, and this irradiation means illuminates the printed circuit board using a light pattern having a sinusoidal (stripe shaped) light intensity distribution. Thereafter, points on the circuit board are measured using a CCD camera or the like disposed directly above the circuit board. In this case, intensity I of light at a point P on the measurement object in the image is given by the following equation:

$$I = e + f \times \cos(\phi)$$

(within the formula, e=direct current optical noise (offset component), f=sine wave contrast (reflectivity), and φ=phase imparted by unevenness of the object).

At this time, the light pattern is moved and the phase is changed, for example, in four stages (e.g., φ+0, φ+π/2, φ+π, and φ+3π/2). Images having intensity distributions corresponding to these phase shift changes (e.g., I0, I1, I2, and I3, respectively) are captured, and the modulation component α is determined based on the formula below.

$$\alpha = \arctan\{(I3-I1)/(I0-I2)\}$$

This modulation component α can be used to determine the three-dimensional coordinates (X, Y, Z) at the point P on the measurement object, such as cream solder or the like, and these three-dimensional coordinates are used to measure the three-dimensional shape of the cream solder and particularly to measure height of the cream solder.

However, actual measurement objects include both tall measurement objects and short measurement objects. For example, in the case of cream solders, there are both thin film-shaped cream solders and protruding cream solders which form a truncated cone shape. If the gaps between the lines of the irradiated light pattern are widened in order to adjust to the maximum height among such measurement objects, resolution ability becomes poor, and there is concern that measurement accuracy will worsen. On the other hand, although attempting to improve accuracy may be possible by narrowing the gaps between the lines, this then results in concern that the height range which is capable of measurement would become insufficient (such narrow gaps would result in errors due differences in line orders).

Therefore, combining the above-described phase shift method with the spatial encoding method has been proposed to obtain a large height range capable of measurement while also attaining highly accurate measurement (e.g., see Patent Citation 2).

Patent Citation 1: Japanese Unexamined Laid-open Patent Application No. H11-211443

Patent Citation 2: Japanese Unexamined Laid-open Patent Application No. H11-148810

However, according to the technology described in Patent Citation 2, a previously determined number of imaging operations must be performed even if the spatial encoding method is used in addition to the phase shift method, and this necessarily invites an increase in the number of imaging operations. For this reason, there has been concern that this technology invites an overall lowering of processing speed and the need for more time during measurement.

In consideration of the above-described circumstances, the object of the present invention is to provide a three-dimensional measuring device and a board inspection device capable of increasing the height range capable of measurement, attaining highly accurate measurement, and suppressing the number of imaging operations to a minimum, thereby attaining an improvement of efficiency of measurement (or inspection).

SUMMARY OF INVENTION

Various aspects of the present invention suited for solving the above-described problem will be described separately below. As may be required, the operational effects and the like may also be described for the corresponding aspect.

A first aspect of the present invention is a three-dimensional measuring device which includes: an irradiation means capable of irradiating a striped light pattern used for a spatial encoding method and a striped light pattern used for a phase shift method on a measurement object part on a board main body; an imaging means capable of imaging a measurement object part irradiated by the light pattern; an image control means for controlling imaging by the imaging means; a first calculation means for calculating at least a height of the measurement object part according to the phase shift method based on a multiplicity of image data imaged by the imaging means; and a second calculation means capable of using the spatial encoding method to identify a line corresponding to the measurement object part from among the image data at a time of calculation by the first calculation means by the phase shift method based on image data imaged by the imaging means, wherein the imaging control means determines an imaging count by the imaging means for irradiation of the light pattern used for the spatial encoding method based on approximate height data or height data of the measurement object part and executes imaging of the determined imaging count.

A second aspect of the present invention is a three-dimensional measuring device which includes: an irradiation means capable of irradiating a striped light pattern used for a spatial encoding method and a striped light pattern used for a phase shift method on a measurement object part on a board main body; an imaging means capable of imaging a measurement object part irradiated by the light pattern; an image control means for controlling imaging by the imaging means; a first calculation means for calculating at least a height of the measurement object part according to the phase shift method based on a multiplicity of image data imaged by the imaging means; and a second calculation means capable of using the spatial encoding method to identify a line corresponding to the measurement object part from among the image data at a time of calculation by the first calculation means by the phase shift method based on image data imaged by the imaging means, wherein the imaging control means obtains height data or approximate height data of the measurement object part based on at least one of measurement data and production data of the board, determines an imaging count for the imaging means for irradiation of the light pattern used for the spatial encoding method based on the height data or the approximate height data of the measurement object part, and executes imaging of the determined imaging count.

According to the first and second aspects of the present invention, at least height of the measurement object part is calculated using the phase shift method by the first calculation means based on a multiplicity of image data imaged by the imaging means. Further, either beforehand or simultaneously therewith, the second calculation means uses the spatial encoding method to identify a line corresponding to the measurement object part from among the image data during calculation by the first calculation means using the phase shift method based on the image data imaged by the imaging means. That is to say, the line corresponding to the measurement object part in the phase shift method is identified (i.e., the line order is identified), and the first calculation means uses this line for calculation of height of the measurement object part by the first calculation means. As a result, it becomes possible to realize both the effects of increasing the height range capable of measurement, which is an advantage of the spatial encoding method, and realizing highly accurate measurement, which is an advantage of the phase shift method.

The imaging control means also controls imaging by the imaging means. Particularly, the imaging control means in the second aspect, based on design data and/or production data of the board, acquires height data or approximate height data of the measurement object part. Further, according to the first and second aspects, based on such height data or approximate height data, the imaging count for the above-described imaging means is determined for irradiation of the light pattern used for the above-described spatial encoding method, and imaging is performed of the determined imaging count. Therefore, when height of the measurement object part is not particularly high, the imaging count by the imaging means for irradiation of the light pattern used for the spatial encoding method can be further reduced. On the other hand, if height of the measurement object part is high, the imaging count of the imaging means for irradiation of the light pattern used for the spatial encoding method is increased accordingly, making it possible to accurately identify the line order for the phase shift method that corresponds with the height range. That is to say, the most appropriate minimum imaging count can be determined according to height data and the like of the measurement object part obtained at a given time, and thus three-dimensional measurement can be realized which has high accuracy using an overall minimum imaging count. As a result, improvement of measurement efficiency can be realized.

A third aspect of the present invention is a three-dimensional measuring device which includes: an irradiation means capable of irradiating a striped light pattern used for a spatial encoding method according to a predetermined coding of light intensity distribution and a striped light pattern used for a phase shift method having a substantially sinusoidal wave shaped light intensity distribution on a measurement object part on a board main body; an imaging means capable of imaging a measurement object part irradiated by the light pattern used for the spatial encoding method and the light pattern used for the phase shift method; an image control means for controlling imaging by the imaging means; a first calculation means for calculating at least a height of the measurement object part by the phase shift method based on a multiplicity of image data imaged by the imaging means; and a second calculation means capable of using the spatial encoding method to identify a line order at a time of calculation by the first calculation means by the phase shift method based on image data imaged by the imaging means, wherein the imaging control means obtains height data or approximate height data of the measurement object part based on at least one of design data and production data of the board, determines an imaging count for the imaging means for irradiation of the light pattern used for the spatial encoding method based on the height data or the approximate height data, and executes imaging of the determined imaging count.

The same fundamental effects as obtained by the above-described first and second aspects are obtained according to the third aspect of the present invention. Specifically, the range of height capable of measurement by the spatial encoding method can be increased, and highly accurate measurement by the phase shift method can be attained. Also, the most appropriate imaging count can be identified according to height data or the like of the measurement object part acquired at a given time, and an improvement of measurement efficiency can be realized.

A forth aspect of the present invention is a three-dimensional measuring device according to any one of the first aspect through third aspect, wherein, when the obtained height data or the approximate height data constitutes data indicating that height of the measurement object part is less than a predetermined first value, the imaging count of the imaging means for irradiation of the light pattern used for the spatial encoding method is set to zero, and the height of the measurement object part is calculated by the first calculation means without identification by the second calculation means.

According to the forth aspect, when height of the measurement object part is less than a predetermined first value, imaging using irradiation of the light pattern for the spatial encoding method is not performed. That is to say, identification processing by the second calculation means is not performed, and height of the measurement object part is calculated only using the phase shift method. Thus, when height of the measurement object part is low, highly accurate measurement is possible without performing imaging for the spatial encoding method. This has the effect of greatly improving efficiency of measurement.

A fifth aspect of the present invention is a three-dimensional measuring device according to any one of the first aspect through forth aspect, wherein, when the obtained height data or the approximate height data constitutes data indicating that height of the measurement object part is greater than or equal to a predetermined first value, the imaging count of the imaging means for irradiation of mutually different light patterns used by the spatial encoding method is set to two or greater.

According to the fifth aspect of the present invention, when height of the measurement object part is greater than or equal to the predetermined first value, the imaging count of the imaging means is set to two or greater for irradiation of mutually different light patterns used by the spatial encoding method. In this manner, performing the imaging two or more times results in two or more image data used for the spatial encoding method. By this means, even when there would be a multiplicity of height candidates when using only the phase shift method, more accurate identification is possible of the line order for the phase shift method, and thus accurate measurement can be attained.

A sixth aspect of the present invention is a three-dimensional measuring device according to any one of the first aspect through fifth aspect, wherein the striped light pattern used for the phase shift method is a pattern having a same period but a different phase for each imaging for irradiation of the striped light pattern used by the phase shift method.

According to the sixth aspect of the present invention, the striped light pattern used for the phase shift method is a pattern that has the same period but a different phase during each of the imaging count imaging operations using imaging of the striped light pattern used for the phase shift method. Therefore, the calculation formulae and calculation program of the phase shift method can be simplified, and accuracy of measurement can be improved.

A seventh aspect of the present invention is a three-dimensional measuring device according to any one of the first aspect through sixth aspect, wherein the striped light pattern used for the spatial encoding method is a pattern in which light and dark reverses at a period that is a multiple of an integer value, the integer value being different for each imaging for irradiation of the light pattern used for the spatial encoding method with respect to a minimum period light pattern.

According to the seventh aspect of the present invention, by increasing the imaging count, the height range capable of measurement can be increased.

An eighth aspect of the present invention is a three-dimensional measuring device according to any one of the first aspect through seventh aspect, wherein the irradiation means is constituted by a single light source and is capable of switching irradiation between the light pattern used for the phase shift method and the light pattern used for the spatial encoding method.

According to the eighth aspect of the present invention, the need for a separate irradiation means for the phase shift method and the spatial encoding method is eliminated, space can be economized, and an increase of cost can be suppressed.

A ninth aspect of the present invention is a three-dimensional measuring device according to any one of the first aspect through eighth aspect, wherein the irradiation means comprises a liquid crystal slit plate and a light source, and, by controlling voltage applied to a multiplicity of electrodes at one face side of the liquid crystal slit plate, the irradiation means is capable of transmitting light from the light source in a substantially sinusoidal shape for irradiation of the striped light pattern for the phase shift method, and transmitting the light from the light source in a striped-shaped manner for irradiation of the light-dark line striped light pattern used for the spatial encoding method.

According to the ninth aspect of the present invention, a liquid crystal slit plate is used, and this liquid crystal slit plate can be used for irradiation for the phase shift method and also irradiation for the spatial encoding method. Therefore, the operational effect described for the eighth aspect is more reliably attained.

A tenth aspect of the present invention is a board inspection device which includes the three-dimensional measuring device according to any one of the first aspect through the ninth aspect.

According to the tenth aspect of the present invention, each of the above-described technical concepts can be embodied in a board inspection device which is equipped with the three-dimensional measuring device.

DETAILED DESCRIPTION

An embodiment will be explained below with reference to the figures.

Figure 1:
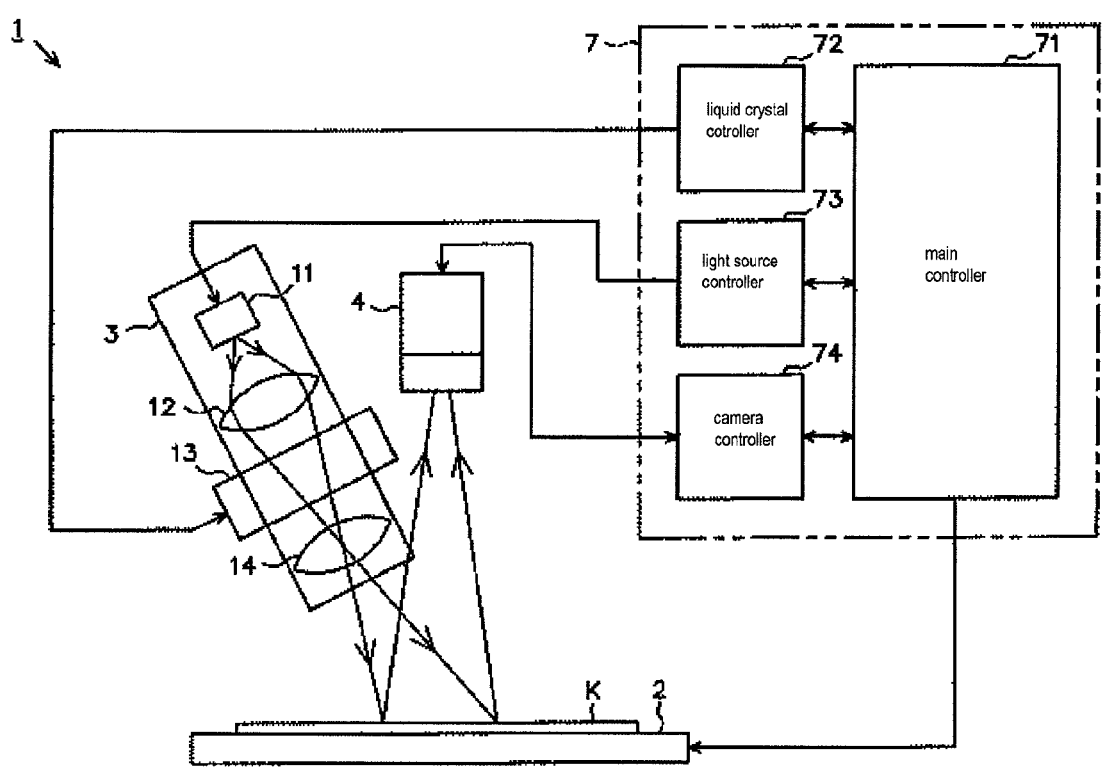
FIG. 1 shows a simplified configuration drawing showing a board inspection device which includes a three-dimensional measurement device.

FIG. 1 is a simplified configuration drawing showing schematically a board inspection device 1 equipped with a three-dimensional measurement device of the present embodiment. As shown in FIG. 1, the board inspection device 1 is equipped with a conveyer 2 for carrying a printed circuit board K printed with a cream solder forming the inspection object, an irradiation means 3 for irradiating a certain light pattern obliquely from above onto the surface of the printed circuit board K, and a CCD camera 4 as an imaging means for imaging a region illuminated by the above-described irradiation on the printed circuit board K. A cream solder C in the present embodiment is formed and printed on an electrode pattern formed from copper foil provided on the printed circuit board K. Further, solder plating is provided on the electrode pattern. The above-described conveyer 2 is configured so as to move the printed circuit board K during inspection in the horizontal direction, i.e., X axis direction and Y axis direction.

The irradiation means 3 will be explained in further detail. The irradiation means 3 is equipped with a light source 11 formed from an LED, a condensing lens 12 for condensing light irradiated from the light source 11, a liquid crystal transmission device 13, and a projection lens 14 for projecting the light pattern transmitted through the liquid crystal transmission device 13.

In the present embodiment, the irradiation means 3 is configured so as to be capable of irradiating while switching between the light pattern used for the phase shift method and the light pattern used for the spatial encoding method. More specifically, the light pattern used for the phase shift method is a striped light pattern having light intensity (luminosity) that varies in a sinusoidal pattern at a fixed period. Phase of this striped light pattern is varied in ¼ pitch increments during irradiation for the phase shift method.

The light pattern used for the spatial encoding method is a pattern in which light and dark areas reverse at a period that is a multiple of an integer that differs during each irradiation count relative to a minimum period light pattern. More specifically, taking the minimum period to be a period (period 1) of the striped light pattern used for the above-described phase shift method, a striped light pattern that reverses from light to dark and vice-versa is irradiated so as to include one light part and one dark part within the period 1. During the second irradiation, a striped light pattern that reverses from light to dark and vice-versa is irradiated so as to include one light part and one dark part within a period that is twice that of the period 1. During the third irradiation, a striped light pattern that reverses from light to dark and vice-versa is irradiated so as to include one light part and one dark part within a period that is four times that of the period 1 (four times the above described minimum period).

Figure 2:
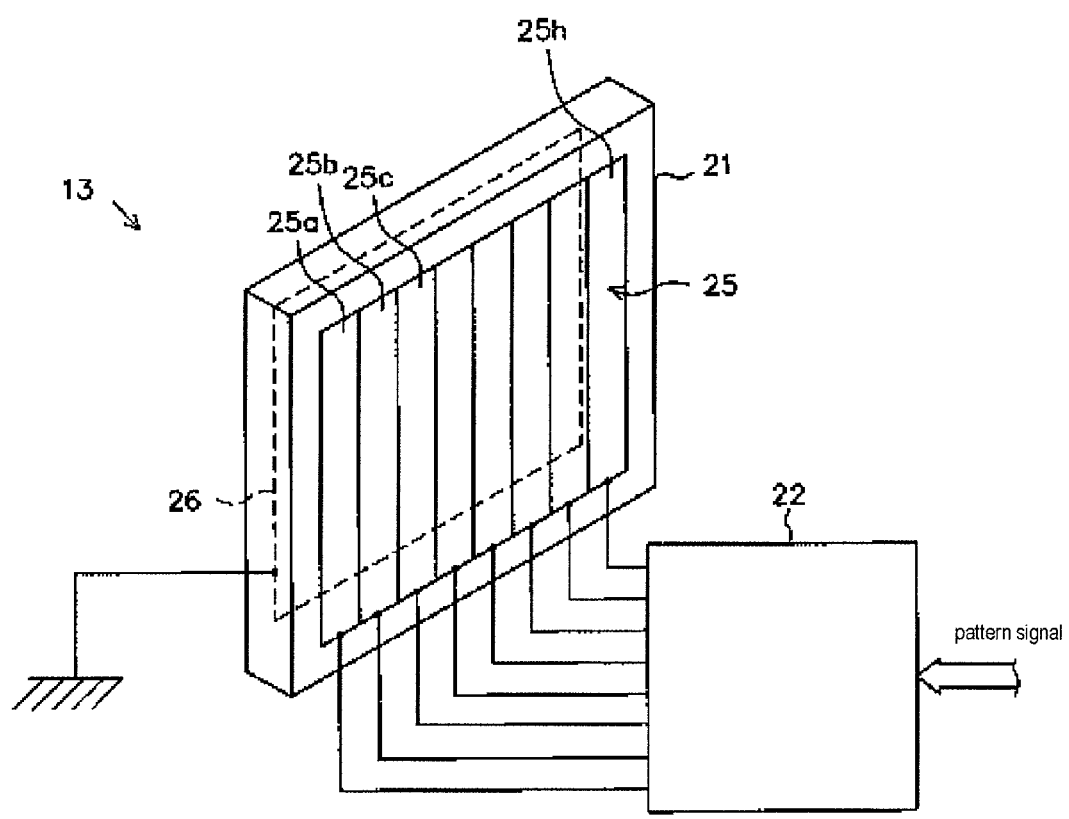
FIG. 2 shows a simplified structural drawing showing a liquid crystal transmission device.

In the present embodiment, in order to attain the irradiation of this type of light pattern, the below-described configuration of the liquid crystal transmission device 13 is adopted. That is to say, as shown in FIG. 2, the liquid crystal transmission device 13 includes a liquid crystal slit plate 21 and a decoder 22 for decoding a pattern signal from a below-described liquid crystal controller 72 of a control device 7 and for changing the slit pattern of the liquid crystal slit plate 21. Provided at one surface of the liquid crystal slit plate 21 is a multiplicity of anode-side transparent electrodes 25a, 25b, 25c, ... 25h (collectively referred to as "anode-side transparent electrodes 25") partitioned in the length-wise direction of FIG. 2. The depiction of electrodes in this FIG. 2 is abbreviated for convenience, and a large number of anode-side transparent electrodes are actually provided. Electrical power is individually provided to each these electrodes by the decoder 22. A single common cathode side transparent electrode 26 is formed on the opposite face of this liquid crystal slit plate 21, and this electrode 26 is grounded. The liquid crystal, which fills the gap between these electrodes 25 and 26, is either a liquid crystal that blocks light when a voltage is applied or a liquid crystal that becomes transparent when a voltage is applied.

Figure 3:
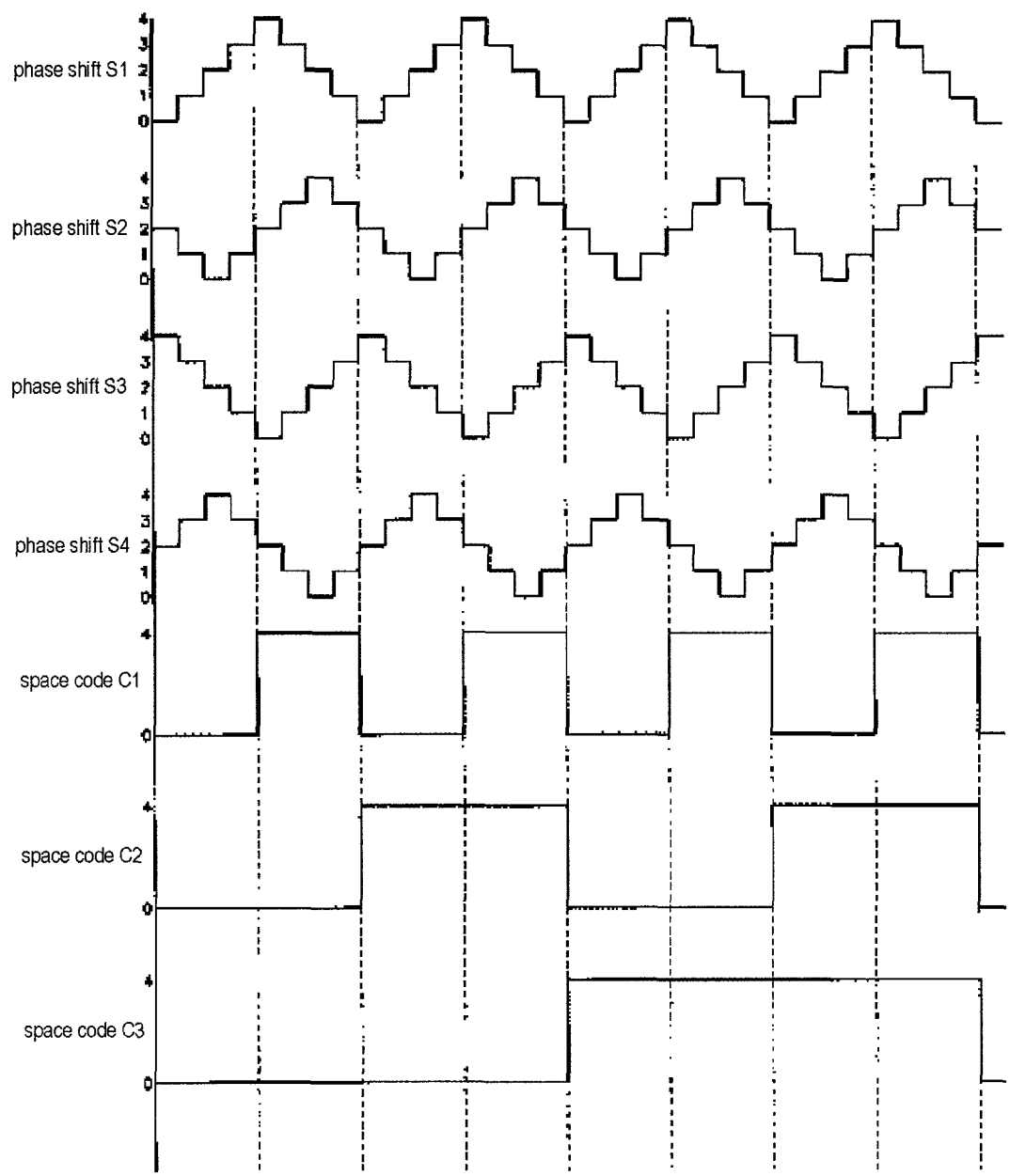
FIG. 3 shows a figure showing the photo-control pattern for the phase shift method and the photo-control pattern for the spatial encoding method in the liquid crystal transmission device.

The photo-control pattern of this liquid crystal transmission device 13 will be explained next. As described previously, the liquid crystal transmission device 13 can be used to switch between a light control pattern used for the phase shift method and a light control pattern used for the spatial encoding method. The photo-control pattern used for the phase shift method, as indicated by the photo-control pattern example of the phase shift S1 through phase shift S4 of FIG. 3, is configured such that light transitivity varies in a stepwise manner such that light is transmitted so as to trace a sine wave. Then, the photo-control pattern is switched, in order, from the phase shift S1 through phase shift S4, and the phase is displaced in 90° (π/2) increments. In this way, the irradiation means 3b irradiates a striped light pattern that varies in a roughly sinusoidal shape at a fixed period, four irradiations are performed, each having a respective phase displaced in the above-described manner, and imaging for the phase shift method is performed for each respective irradiation.

As shown by the photo-control pattern example of spatial code (or space code) C1 through spatial code C3 of FIG. 3, the photo-control pattern used for the spatial encoding method is configured such that light transmission alternates between "0 (minimum)" and "4 (maximum)." Then, for the spatial code C1, a photo-control pattern is used having a stripe shape that reverses so that brightness (light transmission) and darkness (light blockage) each occur once per period 1, where this period 1 is the period (minimum period) of the light transmission pattern of the phase shifts S1 through S4. For the spatial code C2, a photo-control pattern is used having a stripe shape that reverses so that brightness (light transmission) and darkness (light blockage) each occur at a period that is twice the period 1. For the spatial code C3, a photo-control pattern is used having a stripe shape that reverses so that brightness (light transmission) and darkness (light blockage) each occur at a period that is twice as longer (i.e., 4 times that of the spatial code C1).

When measurement by the phase shift method is performed in the present embodiment, four imaging operations are performed for each measurement point. However, as explained below, during measurement by the spatial encoding method, based on the approximate height data of the cream solder at a given time, the imaging count is determined for irradiation of the light pattern used for the spatial encoding method, and imaging and irradiation are performed of the determined imaging count. More specifically, based on the approximate height data of the cream solder, measurement is performed using a first mode if the cream solder (measurement object part) is determined to be within a range such as 0 μm to 100 μm (not including 100 μm). If a determination is made that the measurement object part is within a range such as 100 μm to 200 μm (not including 200 μm), measurement is performed using a second mode. If a determination is made that the measurement object part is within a range such as 200 μm to 400 μm, measurement is performed using a third mode. For convenience of explanation, the present embodiment will be explained for a case in which no cream solder (measurement object part) exceeds 400 μm.

If measurement is performed in the first mode, the imaging count for the spatial encoding method is set to zero. Therefore, in this case, measurement is only performed by the phase shift method.

If measurement is performed in the second mode, the imaging count for the spatial encoding method is set to two. In this case, irradiation is performed using the minimum period spatial code C1 photo-control pattern and the two-fold longer period spatial code C2 photo-control pattern.

If measurement is performed in the third mode, the imaging count for the spatial encoding method is set to three. In this case, irradiation is performed using the minimum period spatial code C1 photo-control pattern, the two-fold longer period spatial code C2 photo-control pattern, and the further two-fold longer spatial code C3 photo-control pattern.

As shown in FIG. 1, the control device 7 is provided for drive control of the above-described irradiation means 3, the CCD camera 4, the conveyer 2, and the like. The control device 7 also performs inspection and various types of calculation (measurement) based on the image data imaged by the CCD camera 4. That is to say, when the printed circuit board K is placed at a certain position on the conveyer 2, the control device 7 firstly performs drive control of a non-illustrated motor or the like to cause movement to a certain position, and the control device 7 causes the printed circuit board K to move to the initial position. This initial position, for example, is one position within a surface of the printed circuit board K that has been partitioned beforehand into units, each the size of a field of the CCD camera 4. The control device 7 also performs drive control of the irradiation means 3, initiating the irradiation of the light pattern, and performs sequential switching control between the four types of irradiation by shifting the light pattern used for the phase shift method in ¼ pitch increments. Further, as may be required, irradiation of the light pattern used for the spatial encoding method may also be performed. While irradiation of light patterns is performed in this manner, the control device 7 also performs drive control of the CCD camera 4, images the inspection area part for each of these irradiations, and obtains the respective required image data (imaging data used for the phase shift method and image data used for the spatial encoding method).

The control device 7 is equipped with an image memory, and stores each of the image data sequentially. The control device 7 performs various types of image processing based on this stored image data. While this image processing is being performed, the control device 7 performs drive control of the motor and causes the conveyer 7 (printed circuit board K) to move to the next inspection area. The control device 7 stores this image data in the image memory. However, once image processing has been completed using the image memory, the next image data is already stored in the image memory, and thus the control device 7 can quickly perform the next image processing. That is to say, while inspection moves to the next inspection area ((n+1)th) and image input is performed, image processing and measurement-determination are performed for the nth inspection area. Thereafter, the above-described parallel processing is repeated similarly until inspection of all of the inspection areas has been completed. While the inspection area is moved due to control by the control device 7 of the board inspection device 1 of the present embodiment in this manner, sequential imaging processing is performed simultaneously, and thus three-dimensional measurement including height measurement of cream solder on the printed circuit board K is performed, making it possible to inspect a printed condition of the cream solder rapidly and accurately.

In order to realize the above-described type of control, the control device 7 is equipped with a main controller 71, a liquid crystal controller 72, a light source controller 73, and a camera controller 74 as the image control means. The liquid crystal controller 72 mainly controls the above-described photo-control pattern of the liquid crystal transmission device 13. The light source controller 73 mainly performs ON/OFF control of the light source 11. The camera controller 74 controls imaging of the inspection area part by the CCD camera 4, as described previously. In addition to execution of imaging, the camera controller 74 is configured so as to be capable of acquiring (reading) approximate height data of the cream solder based on the printed circuit board K design data, production data, or the like. Then, based on this approximate height data, the camera controller 74 determines the imaging count for the CCD camera 4 based on irradiation of the light pattern used for the spatial encoding method in the above-described manner.

In the present embodiment, approximate height of the cream solder (each measurement object part) is obtained based on the acquiring (reading) of library data of the printed circuit board K as the above-described approximate height data. Of course, the library data is not limited to design data and production data of the printed circuit board K. CAD data, mounting data, component data, or any arbitrary combination of such data may be adopted as the library data.

The main controller 17 mainly manages each of the types of control by each of the controllers 72 through 74, controls the conveyer 2, and performs measurement and image processing (measurement by the phase shift method and measurement by the spatial encoding method) based on the image data obtained by imaging. That is to say, the main controller 71 functions as both the first calculation means and the second calculation means of the present invention.

Figure 4:
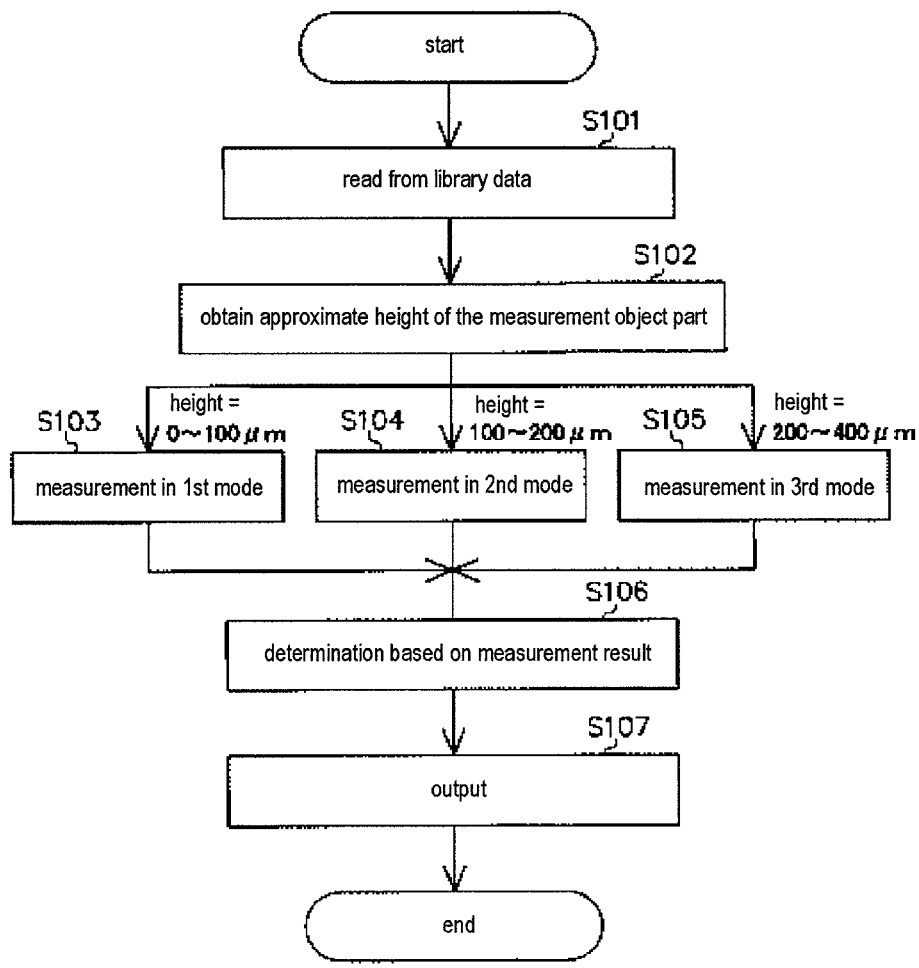
FIG. 4 shows a flowchart showing an example of details of processing of board inspection at a certain inspection area.

Beginning with the main controller 71, the details of processing during three-dimensional measurement (circuit board inspection) by the control device 7 will be explained next using the flow chart of FIG. 4. This FIG. 4 shows an example of processing content of board inspection at a certain inspection area. During step S101, the control device 7 reads the corresponding printed circuit board K library data. In the following step S102, approximate heights of the cream solder (measurement object part) are obtained.

Figure 5:
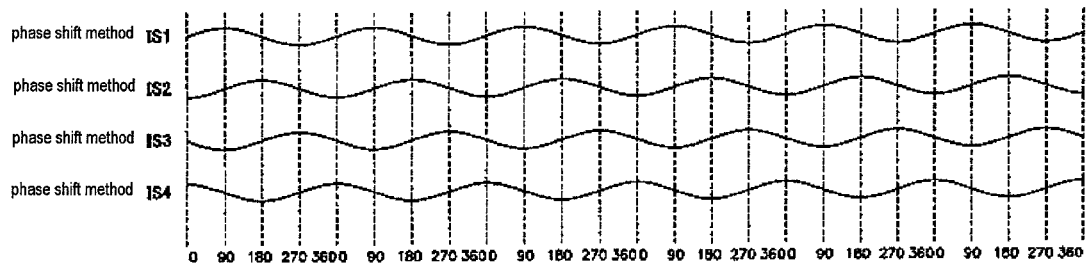
FIG. 5 shows a schematic diagram showing the light pattern for the phase shift method which is irradiated when measuring in the first mode.

Then, if the obtained approximate heights of the measurement object part are within the range of 0 µm to 100 µm, the processing proceeds to step S103, and measurement is performed using the first mode. During measurement using the first mode, as shown in FIG. 5, the imaging count for the spatial encoding method is set to zero. Therefore in this case, measurement is performed only using the phase shift method. That is to say, based on the above-described phase shift S1 through phase shift S4 photo-control patterns, irradiation of light patterns is performed four times (i.e., phase shift method IS1 through phase shift method IS4) as indicated in FIG. 5. Thereafter, height measurement of the measurement object part is performed based only on the phase shift method by a known phase shift method as explained previously in the Background of the Invention.

Figure 6:
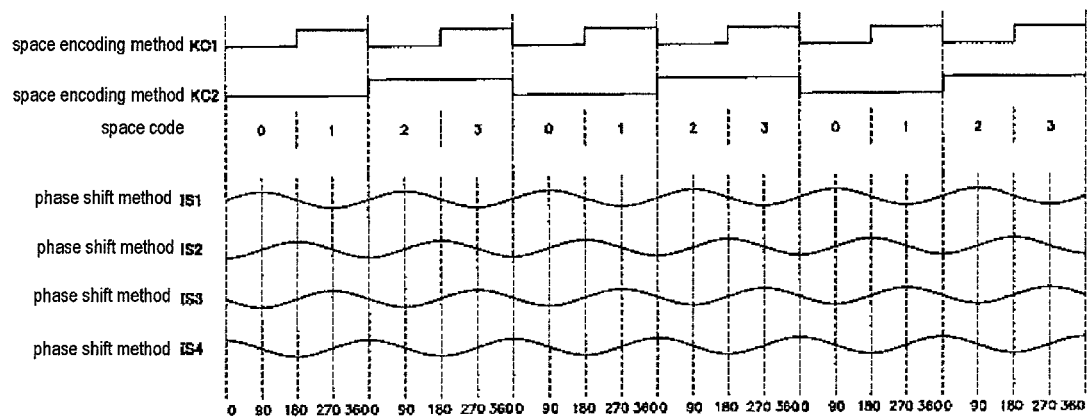
FIG. 6 shows a schematic diagram showing the light pattern for the phase shift method and the light pattern for the spatial encoding method which are irradiated when measuring in the second mode.

If the obtained approximate heights of the measurement object part are within the range of 100 µm to 200 µm, the processing proceeds to step S104, and measurement is performed using the second mode. During measurement using the second mode, the imaging count for the spatial encoding method is set to two. In this case, irradiation is performed using the photo-control patterns of the minimum period spatial code C1 and the spatial code C2 having twice the period of the spatial code C1. That is to say, irradiation is performed twice, as shown in FIG. 6: once using the light pattern of the spatial encoding method KC1 and once using the spatial encoding method KC2, and respective imaging is performed for the spatial encoding method during each of these irradiations. Also, separately from such imaging, irradiation of light patterns is carried out four times (phase shift S1 through phase shift S4), and respective imaging for the phase shift method is performed for each irradiation. Then, based on the spatial encoding method, the spatial code number of the measurement object part is first identified. Based on this spatial code number identification, a line order of the phase shift method is identified. Then, based on the identified line order, the phase shift method is used to perform height measurement of the measurement object part.

Figure 7:
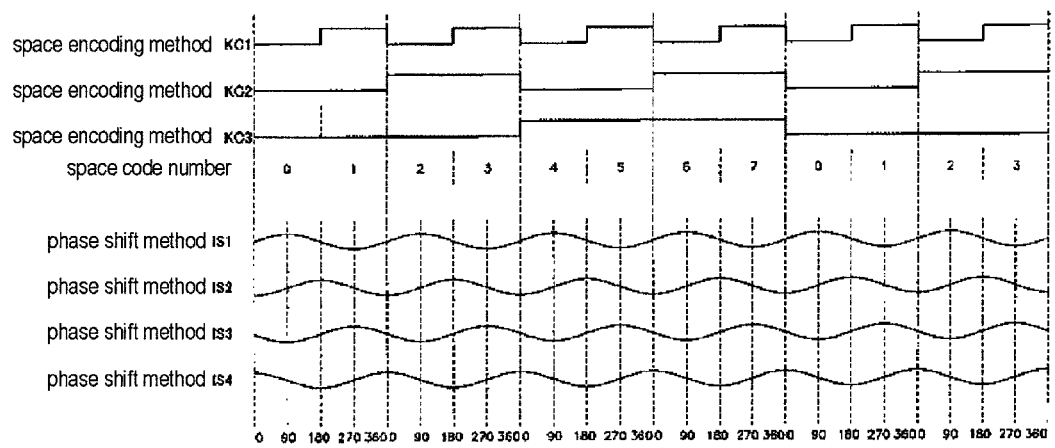
FIG. 7 shows a schematic diagram showing the light pattern for the phase shift method and the light pattern for the spatial encoding method which are irradiated when measuring in the third mode.

If the obtained approximate heights of the measurement object part are within the range of 200 µm to 400 µm, the processing proceeds to step S105, and measurement is performed using the third mode. During measurement using the third mode, the imaging count for the spatial encoding method is set to three. In this case, irradiation is performed using the photo-control patterns of the minimum period spatial code C1, the spatial code C2 having twice the period of the spatial code C1, and the spatial code C3 having twice the period of the spatial code C2. That is to say, irradiation is performed three times, as shown in FIG. 7: once using the light pattern of the spatial encoding method KC1, once using the spatial encoding method KC2, and once using the spatial encoding method KC3, and respective imaging is performed for the spatial encoding method during each of these irradiations. Also, separately from such imaging, irradiations of light patterns are carried out four times, once for each of the phase shift method IS1 through phase shift method IS4, and respective imaging for the phase shift method is performed for each irradiation. Then, based on the spatial encoding method, the spatial code number of the measurement object part is first identified. Based on this spatial code number identification, a line order for the phase shift method is identified. Then, based on the identified line order, the phase shift method is used to perform height measurement of the measurement object part.

After the above-described step S103, step S104, or step S105, a determination based on measurement results occurs during step S106. That is to say, a determination is made as to whether or not the height of the measurement object according to the above-described step S103, step S104, or step 5015 is within a previously set permissible range. Thereafter, this determination result is output externally during step S107. Thereafter, the processing stops. More specifically, when height of the measurement object is within the previously set permissible range, a result of "OK" is output. When the height of the measurement object is not within the permissible range, the result is "failure," and operations are performed such as generation of an alarm sound, emergency stoppage of the inspection device, and display to such effect on a monitor to notify the operator or the like.

Figure 8:
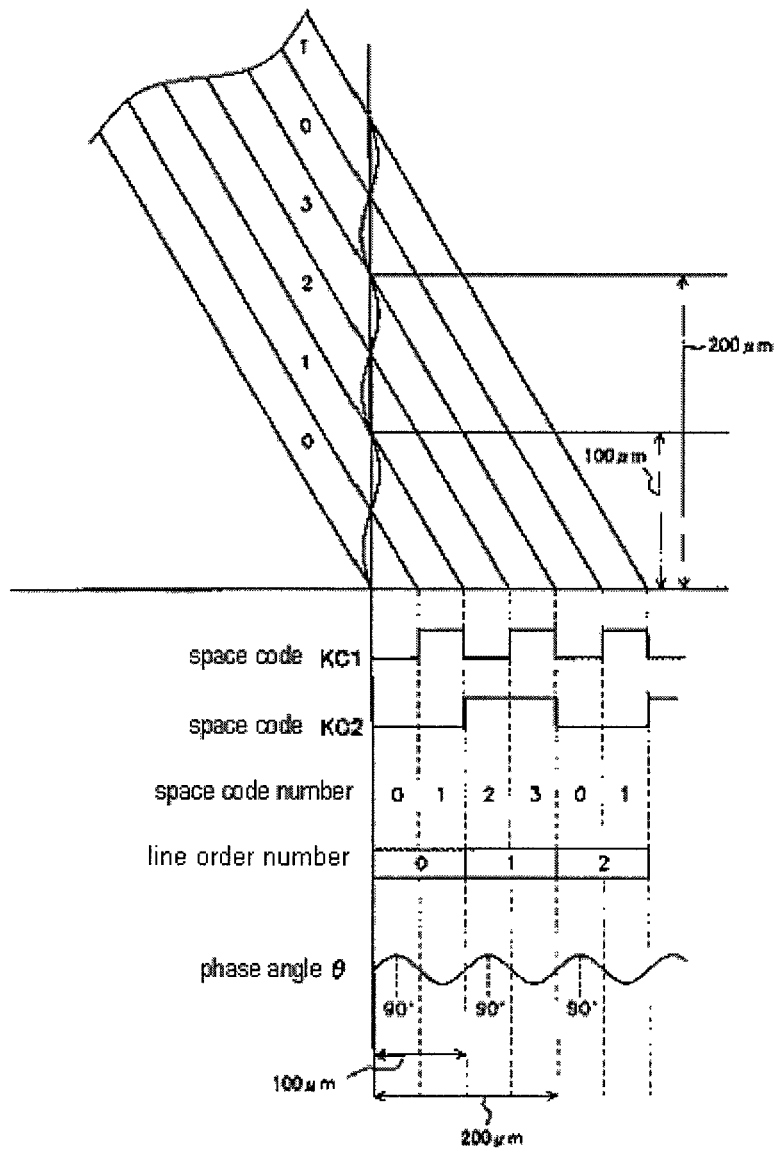
FIG. 8 shows an explanatory drawing showing a specific instance of measurement of height.

A more specific example will be explained next based on FIG. 8. In the above-described manner, final height of the measurement object is determined based on the phase angle θ obtained by the phase shift method. For example, as shown in FIG. 8, one period part of the sine wave in the phase shift method is taken to be 100 μm, and the phase angle θ obtained by the phase shift method is 90°. Then, as shown in FIG. 8, the candidate heights become "25 μm," "125 μm," "225 μm," and so forth. Then, if the approximate height of the measurement object in the library data is estimated to be 100 μm to 200 μm, measurement is performed using the second mode. That is to say, the imaging count for the spatial encoding method is set to two, and light patterns are irradiated twice, once using the spatial encoding method KC1 and once using the spatial encoding method KC2. Respective imaging for the spatial encoding method is performed for each irradiation. Thereafter, if the spatial code number for the spatial encoding method is "0" (if the line order is 0), actual height is taken to be "25 μm." If the spatial code number is "2" (if the line order is 1), the actual height is taken to be "125 μm."

Further, if the phase angle θ obtained by the phase shift method in the above-described example is 180°, the candidate heights per FIG. 8 become "50 μm," "150 μm," "250 μm," and so forth. Then, if the approximate height of the measurement object in the library data is estimated to be 100 μm to 200 μm measurement is performed using the second mode, and the imaging count for the spatial encoding method is set to two. Thereafter, if the spatial code number for the spatial encoding method is "0" or "1" (if the line order is 0 or 2), actual height is taken to be "50 μm." If the spatial code number is "2" or "3" (if the line order is 1), the actual height is taken to be "150 μm."

Figure 9:
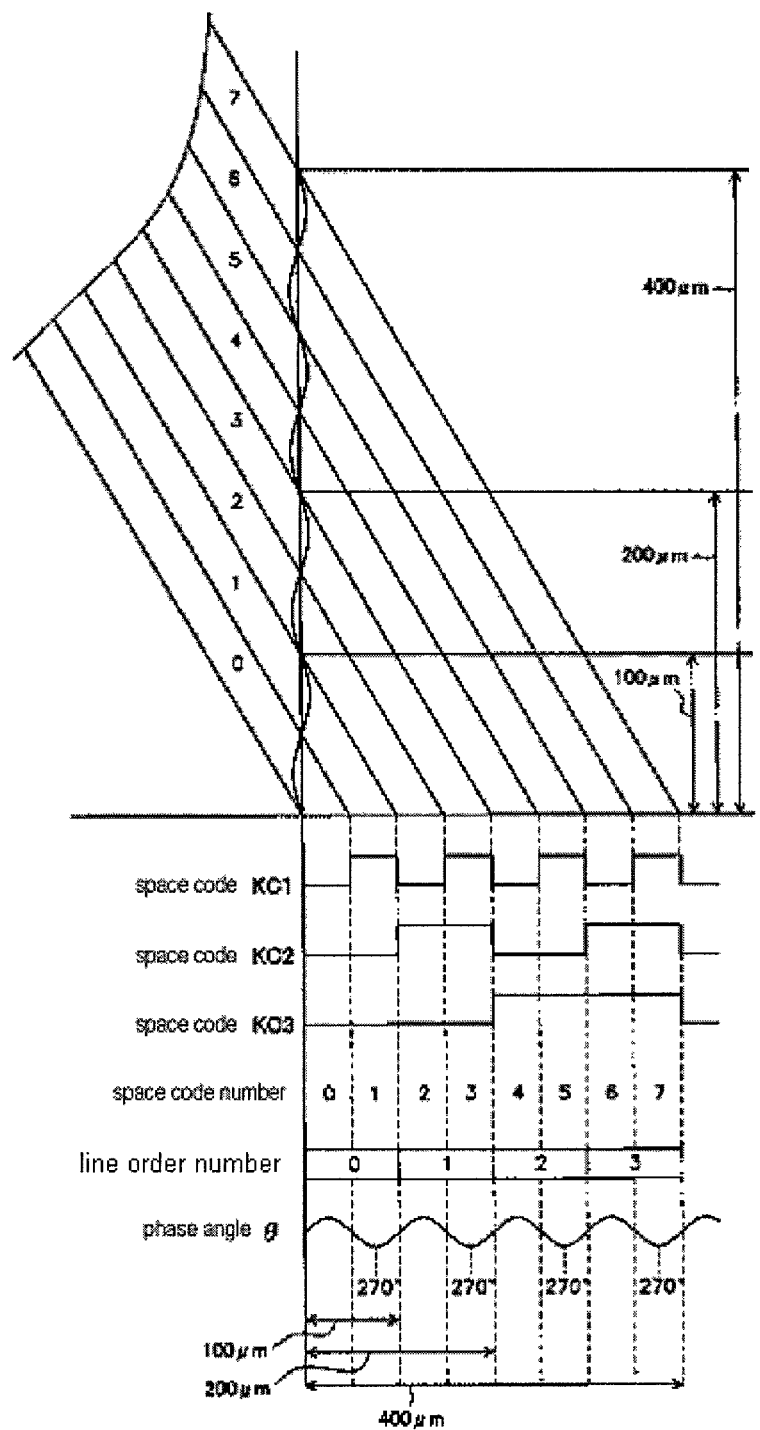
FIG. 9 shows an explanatory drawing showing a different specific instance of measurement of height.

A different example will be explained next. For example, as shown in FIG. 9, if the phase angle θ obtained by the phase shift method is 270° and if one period of a phase shift method sine wave is 100 μm, the candidate heights become "75 μm," "175 μm," "275 μm," "375 μm," and so forth. Then, if the approximate height of the measurement object in the library data is estimated to be 200 μm to 400 μm, measurement is performed using the third mode. That is to say, in this case, the imaging count for the spatial encoding method is set to three, and light patterns are irradiated three times, once using the light pattern of the spatial encoding method KC1, once using the spatial encoding method KC2, and once using the spatial encoding method KC3. Respective imaging is performed for the spatial encoding method during each of these irradiations. Thereafter, if the spatial code number for the spatial encoding method is "1" (if the line order is 0), actual height is taken to "75 μm." If the spatial code number for the spatial encoding method is "3" (if the line order is 1), actual height is taken to "175 μm." If the spatial code number for the spatial encoding method is "5" (if the line order is 2), actual height is taken to "275 μm." If the spatial code number for the spatial encoding method is "7" (if the line order is 3), actual height is taken to "375 μm."

Although measurement of height of the measurement object part is finally taken by the phase shift method according to the present embodiment in the above-described manner, the spatial encoding method is used beforehand to identify the spatial code number corresponding to the line (line order) associated with the measurement object part. That is to say, by identification of the line order, height of the measurement object part is measured. As a result, it becomes possible to realize both the effects of increasing the height range capable of measurement, which is an advantage of the spatial encoding method, and realizing highly accurate measurement, which is an advantage of the phase shift method.

The present embodiment does not merely combine the phase shift method and the spatial encoding method, but rather, the present embodiment obtains approximate heights by reading library data and using such approximate heights to determine the imaging count used for the spatial encoding method. More specifically, when approximate height of the measurement object part is within the range of 0 μm to 100 measurement is executed using the first mode (phase shift method alone). When approximate height of the measurement object part is within the range of 100 μm to 200 μm, measurement is executed using the second mode (two imaging operations using the phase shift method and the spatial encoding method). When approximate height of the measurement object part is within the range of 20 μm to 400 μm, measurement is executed using the third mode (three imaging operations using the phase shift method and the spatial encoding method). In this manner, when the various measurement object parts are not particularly high, the imaging count of the imaging means for irradiation of the light pattern used for the spatial encoding method can be set to a lower value. On the other hand, if height of the measurement object part is high, the imaging count of the imaging means for irradiation of the light pattern used for the spatial encoding method is increased accordingly, making it possible to accurately identify the spatial code number (line order for the phase shift method) that corresponds with the height range. That is to say, the most appropriate minimum imaging count can be determined according to height data and the like of the measurement object part obtained at a given time, and thus three-dimensional measurement can be realized which has high accuracy using an overall minimum imaging count. As a result, improvement of measurement efficiency can be realized.

Particularly, when the approximate height of the measurement object part is within the range of 0 μm to 100 μm, according to the present embodiment, the imaging count for irradiation of the light pattern used for the spatial encoding method is set to zero, and height measurement of the measurement object part is performed only by the phase shift method. Therefore, a greater improvement of measurement efficiency can be realized.

On the other hand, when the approximate height of the measurement object part is greater than or equal to 100 μm, the imaging count is set to two or greater for irradiation of mutually different light patterns using the spatial encoding method. In this manner, due to performance of two or more imaging operations, two or more imaging data are present for use in the spatial encoding method. In this way, even where multiple height candidates would exist if the phase shift method had been used alone, this embodiment makes it possible to identify the line order for the phase shift method with greater accuracy, whereby accurate measurements can be realized.

Further, according to the present embodiment, a single irradiation means 3 and a single CCD camera 4 are used. In other words, imaging is possible without use of a separate imaging means for the phase shift method and the spatial encoding method, and irradiation is possible without use of separate irradiation means for the phase shift method and the spatial encoding method. Therefore, the required space can be reduced, and cost increase can be suppressed. Also, according to the present embodiment, the liquid crystal transmission device 13 having the liquid crystal slit plate 21 is used as the irradiation means 3, and thus application is possible for both irradiation for the phase shift method and irradiation for the spatial encoding method. This has the effect of making the above-described operational effects more reliable.

The present invention is not limited to the details of the above-described embodiment, and the present invention may be implemented, for example, in the below-described manners.

(a) The above-described embodiment describes a case in which height of the cream solder (measure object part) does not exceed 400 μm. However, by further increasing the imaging count for the spatial encoding method, measurement is possible even if this height exceeds 400 μm. That is to say, although the upper limit of the imaging count for the spatial encoding method is three in the above-described embodiment, there is no obstacle to performing four or more imaging operations.

Figure 10:
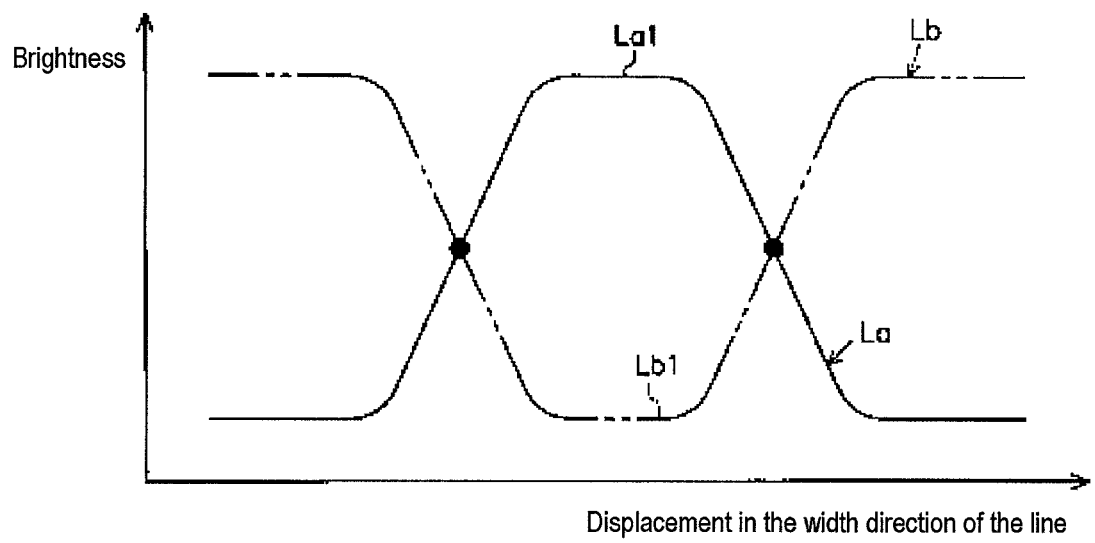
FIG. 10 shows an explanatory drawing showing an instance of determination of the light-dark boundary by separate irradiation of light patterns which has inverted lightness and darkness area in the photo-control patterns using the liquid crystal transmission device in a separate embodiment.

(b) Although not mentioned particularly in the above-described embodiment, identification of the light-dark boundary is important in the spatial encoding method. Therefore, the liquid crystal transmission device 13 may irradiate separately photo-control patterns having inverted light-dark light patterns. In this manner, the first light pattern is used for imaging, and a second light pattern having reversed light-dark irradiation regions of this first light pattern is used for imaging. In FIG. 10, part of the image data obtained by irradiation of the first light pattern is indicated by the designation La, and part of the image data obtained by irradiation of the second light pattern is indicated by the designation Lb. The part La1 of the irradiation region corresponding to the transmitted light region of the image data La obtained using the first light pattern becomes the part Lb1 corresponding to the shaded (dark) region of the image data Lb when using the second light pattern. By taking the points of mutual intersecting brightness of these image data La and Lb (points of mutually intersecting light intensity) to be the boundary of lightness and darkness, even if irregularities appear in the light from the light source, or if external factors are present, such problems have no effect, and accurate identification of the light-dark boundary is possible. As a result, accurate calculation by the spatial encoding method can be attained.

(c) Although imaging count by the phase shift method is taken to be four times in the above-described embodiment, this imaging count may be set to three (see Japanese Unexamined Laid-open Patent Application No. 2002-81924).

(d) Although measurement in the above-described embodiment is performed using a minimum period of 100 μm, this value is only illustrative, and there is no particular limitation to the value.

(e) Although cream solder is the measurement object in the above-described embodiment, measurement may also be performed on other measurement objects. Other measurement objects may be, for example, solder bumps, electronic components, or the like.

(f) Although a measured height deviated from the range for even a single instance was determined to be a failure in the above-described embodiment, no limitation is placed on the determination standard. For example, a determination of failure may be made when a multiplicity of areas deviate, and a determination of failure may be made when the volume of the entire cream solder is less than or equal to a predetermined value.

DESCRIPTION OF REFERENCE NUMERALS

1 . . . board inspection device
3 . . . irradiation means
4 . . . CCD camera forming the imaging means
7 . . . control device
11 . . . light source
12 . . . liquid crystal transmission device
21 . . . liquid crystal slit plate
25, 26 . . . electrode
71 . . . main controller
72 . . . liquid crystal controller
73 . . . light source controller
74 . . . camera control as the imaging control means

What is claimed is:
1. A three-dimensional measuring device comprising:
an irradiation means capable of irradiating a striped light pattern used for a spatial encoding method and a striped light pattern used for a phase shift method on a measurement object part on a board main body;
an imaging means capable of imaging a measurement object part irradiated by the light pattern;
an image control means for controlling imaging by the imaging means;
a first calculation means for calculating at least a height of the measurement object part according to the phase shift method based on a multiplicity of image data imaged by the imaging means; and
a second calculation means capable of using the spatial encoding method to identify a line corresponding to the measurement object part from among the image data at a time of calculation by the first calculation means by the phase shift method based on the image data imaged by the imaging means,
wherein the imaging control means determines an imaging count for the imaging means for irradiation of the light pattern used for the spatial encoding method based on height data or approximate height data of the measurement object part and executes imaging of the determined imaging count, and wherein, when the obtained height data or the approximate height data constitutes data indicating that the height of the measurement object part is less than a predetermined first value, the imaging count of the imaging means for irradiation of the light pattern used for the spatial encoding method is set to zero, and the height of the measurement object part is calculated by the first calculation means without identification processing by the second calculation means.

2. A three-dimensional measuring device comprising:
an irradiation means capable of irradiating a striped light pattern used for a spatial encoding method and a striped light pattern used for a phase shift method on a measurement object part on a board main body;
an imaging means capable of imaging a measurement object part irradiated by the light pattern;
an image control means for controlling imaging by the imaging means;
a first calculation means for calculating at least a height of the measurement object part according to the phase shift method based on a multiplicity of image data imaged by the imaging means; and
a second calculation means capable of using the spatial encoding method to identify a line corresponding to the measurement object part from among the image data at a time of calculation by the first calculation means by the phase shift method based on the image data imaged by the imaging means,
wherein the imaging control means obtains height data or approximate height data of the measurement object part based on at least one of measurement data and production data of the board, determines an imaging count for the imaging means for irradiation of the light pattern used for the spatial encoding method based on the height data or the approximate height data of the measurement object part, and executes imaging of the determined imaging count, and
wherein, when the obtained height data or the approximate height data constitutes data indicating that the height of the measurement object part is less than a predetermined first value, the imaging count of the imaging means for irradiation of the light pattern used for the spatial encoding method is set to zero, and the height of the measurement object part is calculated by the first calculation means without identification processing by the second calculation means.

3. A three-dimensional measuring device comprising:
an irradiation means capable of irradiating a striped light pattern used for a spatial encoding method according to a predetermined coding of light intensity distribution and a striped light pattern used for a phase shift method having an substantially sinusoidal wave shaped light intensity distribution on a measurement object part on a board main body;
an imaging means capable of imaging a measurement object part irradiated by the light pattern used for the spatial encoding method and the light pattern used for the phase shift method;
an image control means for controlling imaging by the imaging means;
a first calculation means for calculating at least a height of the measurement object part by the phase shift method based on a multiplicity of image data imaged by the imaging means; and
a second calculation means capable of using the spatial encoding method to identify a line order at a time of calculation by the first calculation means by the phase shift method based on the image data imaged by the imaging means,
wherein the imaging control means obtains height data or approximate height data of the measurement object part based on at least one of design data and production data of the board, determines an imaging count for the imaging means for irradiation of the light pattern used for the spatial encoding method based on the height data or the approximate height data and executes imaging of the determined imaging count, and
wherein, when the obtained height data or the approximate height data constitutes data indicating that the height of the measurement object part is less than a predetermined first value, the imaging count of the imaging means for irradiation of the light pattern used for the spatial encoding method is set to zero, and the height of the measurement object part is calculated by the first calculation means without identification processing by the second calculation means.

4. The three-dimensional measuring device as set forth in claim 1,
wherein, when the obtained height data or the approximate height data constitutes data indicating that the height of the measurement object part is greater than or equal to a predetermined first value, the imaging count of the imaging means for irradiation of mutually different light patterns used by the spatial encoding method is set to two or greater.

5. A three-dimensional measuring device comprising:
an irradiation means capable of irradiating a striped light pattern used for a spatial encoding method and a striped light pattern used for a phase shift method on a measurement object part on a board main body;
an imaging means capable of imaging a measurement object part irradiated by the light pattern;
an image control means for controlling imaging by the imaging means;
a first calculation means for calculating at least a height of the measurement object part according to the phase shift method based on a multiplicity of image data imaged by the imaging means; and
a second calculation means capable of using the spatial encoding method to identify a line corresponding to the measurement object part from among the image data at a time of calculation by the first calculation means by the phase shift method based on the image data imaged by the imaging means;
wherein the imaging control means determines an imaging count for the imaging means for irradiation of the light pattern used for the spatial encoding method based on height data or approximate height data of the measurement object part and executes imaging of the determined imaging count, and
wherein, when the obtained height data or the approximate height data constitutes data indicating that the height of the measurement object part is greater than or equal to a predetermined first value, the imaging count of the imaging means for irradiation of mutually different light patterns used by the spatial encoding method is set to two or greater.

6. A three-dimensional measuring device comprising:
an irradiation means capable of irradiating a striped light pattern used for a spatial encoding method and a striped light pattern used for a phase shift method on a measurement object part on a board main body;
an imaging means capable of imaging a measurement object part irradiated by the light pattern;
an image control means for controlling imaging by the imaging means;
a first calculation means for calculating at least a height of the measurement object part according to the phase shift method based on a multiplicity of image data imaged by the imaging means; and
a second calculation means capable of using the spatial encoding method to identify a line corresponding to the measurement object part from among the image data at a time of calculation by the first calculation means by the phase shift method based on image data imaged by the imaging means,
wherein the imaging control means obtains height data or approximate height data of the measurement object part based on at least one of measurement data and production data of the board, determines an imaging count for the imaging means for irradiation of the light pattern used for the spatial encoding method based on the height data or the approximate height data of the measurement object part, and executes imaging of the determined imaging count, and
wherein, when the obtained height data or the approximate height data constitutes data indicating that the height of the measurement object part is greater than or equal to a predetermined first value, the imaging count of the imaging means for irradiation of mutually different light patterns used by the spatial encoding method is set to two or greater.

7. A three-dimensional measuring device comprising:
an irradiation means capable of irradiating a striped light pattern used for a spatial encoding method according to a predetermined coding of light intensity distribution and a striped light pattern used for a phase shift method having a substantially sinusoidal wave shaped light intensity distribution on a measurement object part on a board main body;
an imaging means capable of imaging a measurement object part irradiated by the light pattern used for the spatial encoding method and the light pattern used for the phase shift method;
an image control means for controlling imaging by the imaging means;
a first calculation means for calculating at least a height of the measurement object part by the phase shift method based on a multiplicity of image data imaged by the imaging means; and
a second calculation means capable of using the spatial encoding method to identify a line order at a time of calculation by the first calculation means by the phase shift method based on image data imaged by the imaging means,
wherein the three-dimensional measuring device is configured to calculate the height of the measurement object part using the first calculation means based on identification by the second calculation means of the line order used at the time of calculation by the first calculation means by the phase shift method,
wherein the imaging control means obtains height data or approximate height data of the measurement object part based on at least one of design data and production data of the board, determines an imaging count for the imaging means for irradiation of the light pattern used for the spatial encoding method based on the height data or the approximate height data, and executes imaging of the determined imaging count, and
wherein, when the obtained height data or the approximate height data constitutes data indicating that the height of the measurement object part is greater than or equal to a predetermined first value, the imaging count of the imaging means for irradiation of mutually different light patterns used by the spatial encoding method is set to two or greater.

8. The three-dimensional measuring device as set forth in claim 1,
wherein the striped light pattern used for the phase shift method is a pattern having a same period but a different phase for each imaging for irradiation of the striped light pattern used by the phase shift method.

9. The three-dimensional measuring device as set forth in claim 1,
wherein the striped light pattern used for the spatial encoding method is a pattern in which light and dark reverses at a period that is a multiple of an integer value, the integer value being different for each imaging for irradiation of the light pattern used for the spatial encoding method with respect to a minimum period light pattern.

10. The three-dimensional measuring device as set forth in claim 1,
wherein the irradiation means is constituted by a single light source and is capable of switching irradiation between the light pattern used for the phase shift method and the light pattern used for the spatial encoding method.

11. The three-dimensional measuring device as set forth in claim 1,
wherein the irradiation means comprises a liquid crystal slit plate and a light source, and wherein, by controlling voltage applied to a multiplicity of electrodes at one face side of the liquid crystal slit plate, the irradiation means is capable of transmitting light from the light source in a substantially sinusoidal shape for irradiation of the striped light pattern for the phase shift method, and transmitting the light from the light source in a striped-shaped manner for irradiation of the light-dark line striped light pattern used for the spatial encoding method.

12. A board inspection device comprising the three-dimensional measuring device as set forth in claim 1.

13. A board inspection device comprising the three-dimensional measuring device as set forth in claim 8.

14. The three-dimensional measuring device as set forth in claim 2,
wherein, when the obtained height data or the approximate height data constitutes data indicating that the height of the measurement object part is greater than or equal to a predetermined first value, the imaging count of the imaging means for irradiation of mutually different light patterns used by the spatial encoding method is set to two or greater.

15. The three-dimensional measuring device as set forth in claim 3,
wherein, when the obtained height data or the approximate height data constitutes data indicating that the height of the measurement object part is greater than or equal to a predetermined first value, the imaging count of the imaging means for irradiation of mutually different light patterns used by the spatial encoding method is set to two or greater.

16. The three-dimensional measuring device as set forth in claim 2,
wherein the striped light pattern used for the phase shift method is a pattern having a same period but a different phase for each imaging for irradiation of the striped light pattern used by the phase shift method.

17. The three-dimensional measuring device as set forth in claim 3,
wherein the striped light pattern used for the phase shift method is a pattern having a same period but a different phase for each imaging for irradiation of the striped light pattern used by the phase shift method.

18. The three-dimensional measuring device as set forth in claim 5,
wherein the striped light pattern used for the phase shift method is a pattern having a same period but a different phase for each imaging for irradiation of the striped light pattern used by the phase shift method.

19. The three-dimensional measuring device as set forth in claim 6,
wherein the striped light pattern used for the phase shift method is a pattern having a same period but a different phase for each imaging for irradiation of the striped light pattern used by the phase shift method.

20. The three-dimensional measuring device as set forth in claim 7,
wherein the striped light pattern used for the phase shift method is a pattern having a same period but a different phase for each imaging for irradiation of the striped light pattern used by the phase shift method.

* * * * *